United States Patent
Abrams et al.

[11] Patent Number: 6,036,720
[45] Date of Patent: Mar. 14, 2000

[54] SHEET METAL ANEURYSM NECK BRIDGE

[75] Inventors: Robert M. Abrams; Daniel R. Kurz, both of Sunnyvale, Calif.

[73] Assignee: Target Therapeutics, Inc., Fremont, Calif.

[21] Appl. No.: 08/990,314

[22] Filed: Dec. 15, 1997

[51] Int. Cl.⁷ .................................................. A61B 17/08
[52] U.S. Cl. ......................... 606/213; 606/215; 606/200
[58] Field of Search ................................. 606/113, 114, 606/115, 151, 152, 153, 200, 32, 192–198, 213, 214, 215; 623/11–15

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,710,192 | 12/1987 | Liotta et al. . |
| 4,739,768 | 4/1988 | Engelson . |
| 4,994,069 | 2/1991 | Ritchart et al. . |
| 5,108,420 | 4/1992 | Marks . |
| 5,122,136 | 6/1992 | Guglielmi et al. ......................... 606/32 |
| 5,133,733 | 7/1992 | Rasmussen et al. . |
| 5,192,301 | 3/1993 | Kamiya et al. . |
| 5,226,911 | 7/1993 | Chee et al. . |
| 5,242,462 | 9/1993 | El-Nounou et al. . |
| 5,250,071 | 10/1993 | Palermo . |
| 5,258,042 | 11/1993 | Mehta . |
| 5,261,916 | 11/1993 | Engelson . |
| 5,334,217 | 8/1994 | Das ......................................... 606/213 |
| 5,350,399 | 9/1994 | Erlebacher et al. . |
| 5,354,295 | 10/1994 | Guglielmi et al. . |
| 5,356,432 | 10/1994 | Rutkow et al. .......................... 606/213 |
| 5,405,379 | 4/1995 | Lane . |
| 5,425,744 | 6/1995 | Fagan et al. . |
| 5,451,235 | 9/1995 | Lock et al. . |
| 5,593,422 | 1/1997 | Muijs Van de Moer et al. . |
| 5,624,449 | 4/1997 | Pham et al. . |
| 5,634,936 | 6/1997 | Linden et al. . |
| 5,643,317 | 7/1997 | Pavenik et al. . |
| 5,690,666 | 11/1997 | Berenstein et al. . |
| 5,741,297 | 4/1998 | Simon ...................................... 606/215 |
| 5,879,366 | 3/1999 | Shaw et al. .............................. 606/213 |

FOREIGN PATENT DOCUMENTS

| | | |
|---|---|---|
| 0 820 726 A2 | 1/1998 | European Pat. Off. . |
| WO 97/48351 | 12/1997 | WIPO . |

*Primary Examiner*—Michael Buiz
*Assistant Examiner*—Yen Ngo
*Attorney, Agent, or Firm*—Morrison, Foerster, L.L.P.

[57] ABSTRACT

This is a device for bridging the necks of wide-necked or narrow-necked aneurysms in the vasculature. It is a device which may be used by itself to bridge the neck of an aneurysm or used to stabilize the presence of other vaso-occlusive devices such as helically wound coils in that aneurysm. The included vaso-occlusive devices may be delivered to the aneurysm in a variety of different ways, e.g., by a core wire which is linked to the coils by an electrolytically severable or mechanically detachable joint. The vaso-occlusive devices may also be simply pushed into the aneurysm. The aneurysm neck bridge may also be delivered in a variety of ways, but preferably is attached to an electrolytically severable joint for its deployment. The inventive neck bridge may contain one or two sections: a first or inner section to be placed within the aneurysm and an optional second or outer section suitably placed outside the aneurysm. The first section typically has a number of array elements which are intended to be resident within the aneurysm after the device is deployed from the distal end of a catheter. The optional second or outer section has one or more array elements which are to be placed outside the aneurysm. The array elements typically extend from and are attached to an attachment area, often centrally located. The inventive device is at least partially formed of thin, usually metallic, sheets. After deployment of this retainer, the aneurysm may be partially filled with vaso-occlusive devices such as helically wound coils.

11 Claims, 7 Drawing Sheets

SHEET METAL ANEURYSM NECK BRIDGE

BACKGROUND OF THE INVENTION

Different implantable medical devices have been developed for treating a number of ailments associated with body lumens. In particular, occlusive devices are useful in filling vascular or other body spaces. Some body spaces, such as vascular aneurysms, are formed due to a weakening in the wall of an artery. Often these aneurysms are the site of internal bleeding and, catastrophically, the site of strokes. A variety of different embolic agents are known as, at least arguably, suitable for treatment of these openings. These treatments are commonly known as "artificial vaso-occlusion."

One such class of embolic agents includes injectable fluids or suspensions, such as microfibrillar collagen, various polymeric beads, and polyvinylalcohol foam. These polymeric agents may additionally be crosslinked (sometimes in vivo) to extend the persistence of the agent at the vascular site. These agents are often introduced into the vasculature through a catheter. After such introduction, materials there form a solid space-filling mass. Although some provide for excellent short term occlusion, many are thought to allow vessel recanalization due to absorption of polymer into the blood. Another procedure in which a partially hydrolyzed polyvinylacetate (PVA) is dissolved in an ethanol solvent and injected into a desired vascular site is found in Park et al. (attorney docket no. 29025-20112.00) U.S. patent application Ser. No. 08/734,442, filed Oct. 17, 1996, for "LIQUID EMBOLIC AGENTS".

Other materials such as hog hair and suspensions of metal particles have also been suggested and used by those wishing to form occlusions.

Other materials including polymer resins, typically cyanoacrylates, are also employed as injectible vaso-occlusive materials. These resins are typically mixed with a radio-opaque contrast material or are made radio-opaque by the addition of a tantalum powder. Their use is fraught with problems in that placement of the mixture is quite difficult. These materials are ones which crosslink with the human body. Inadvertent embolisms in normal vasculature (due to the inability of controlling the destination of the resins) is not uncommon. The material is also difficult or impossible to retrieve once it has been placed in the vasculature.

Over the past few years, advancements in the artificial occlusions of vessels and aneurysms have occurred due to the delivery and implantation of metal coils as vaso-occlusive devices. Implantable metal coils that are useful as artificial occlusion devices in vasculature lumens or aneurysms are herein referred to as "vaso-occlusions coils."

Vaso-occlusions coils are generally constructed of a wire, usually made of a metal or metal alloy, that is wound to a helix. Many such devices are introduced to the selected target site through a catheter in a stretched linear form. The vaso-occlusive device assumes an irregular shape upon discharge of the device from the distal end of the catheter a variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils used prior to that time, Ritchart taught a coil which is fairly soft and is delivered to the site using a pusher within a catheter lumen. Upon discharge from the delivery catheter, the coil may undertake any of the number of random or regular configurations used to fill the site. The coils are used for small vessel sites, e.g., 0.5–6 mm in diameter. The coils themselves are described as being between 0.010 and 0.030 inches in diameter. The length of the coil wire is typically 15 to 20 times the diameter of the vessel to be occluded. The wire used to make up the coils may be, for instance, 0.002 to 0.006 inches in diameter. Tungsten, platinum, and gold threads or wires are said to be preferred. These coils have a variety of benefits including the fact that they are relatively permanent, they may be easily imaged radiographically, they may be located at a well defined vessel site, and they can be retrieved.

It is common that these vaso-occlusive devices be delivered through microcatheters such as the type disclosed in U.S. Pat. No. 4,739,768, to Engelson. These microcatheters track a guidewire to a point just proximal or within the desired site for occlusion. The coil is advanced through the microcatheter (once the guidewire is removed) and out the distal end hole so to at least partially fill the selected space and create an occlusion.

In addition to vaso-occlusion devices or coils having predetermined secondary shapes that dictate in part their space filling mechanism, other vaso-occlusive coils have been disclosed that take on random shapes when expelled from a delivery sheath. One such type is a vaso-occlusive coil often referred to as "a liquid coil". One example of such a vaso-occlusive coil is disclosed in U.S. Pat. No. 5,690,666, to Berenstein et al. This patent describes a very soft and flexible coil which is flow-injectable through a delivery catheter using, e.g., saline solution.

In addition to the various types of space filling mechanisms and geometries of vaso-occlusive coils, other particularized features of coil designs, such as mechanisms for delivering vaso-occlusive coils through delivery catheters and implanting them in a desired occlusion site, have also been described. The examples of categories of vaso-occlusive coils based upon their delivery mechanisms include pushable coils, mechanically detachable coils, and electrolytically detachable coils.

One example of the type of vaso-occlusive coil referred to above as the "pushable coil" is disclosed in Ritchart et al., discussed above. Pushable coils are commonly provided in a cartridge and are pushed or "plunged" from the cartridge into a delivery catheter lumen. A pusher advances the pushable coil through and out of the delivery catheter lumen and into the site for occlusion.

Mechanically detachable vaso-occlusive devices are typically integrated with a pusher rod and are mechanically detached from the distal end of that pusher after exiting a delivery catheter. Examples of such mechanically detachable vaso-occlusive coils are found in U.S. Pat. No. 5,261,916 to Engelson or U.S. Pat. No. 5,250,071 to Palermo.

Finally, examples of electrolytically detachable vaso-occlusive devices may be found in U.S. Pat. Nos. 5,122,136 and 5,354,295, each to Guglielmi et al. In these devices, the vaso-occlusive portion of the assembly is attached to a pusher via a small electrolytically severable joint. The electrolytically severable joint is severed by the placement of an appropriate voltage on the core wire. The joint erodes in preference either to the vaso-occlusive device itself or to the pusher core wire. The core wire is often simply insulated to prevent the electrolytic response caused by the imposition of electrical current.

Further improvement upon the electrolytical detachment mechanism described just is found in U.S. patent application Ser. No. 08/205,512, filed Mar. 3, 1994. This document describes superimposing a modest alternating current upon the direct current signal. A sensing circuit monitors the alternating current as an indicator of the progression of coil detachment.

Improvements in enhancing the thrombogenic or other occlusive tissue response to metal coils has also been disclosed. For example, vaso-occlusive coils having fibers attached thereto are known—see, for example, U.S. Pat. No. 5,226,911 to Chee et al.

Each of the devices described above may be used in the treatment by occlusion of aneurysms. As noted above, aneurysms present particularly acute medical risk due to the dangers of potential rupture of the thin wall inherent in such an aneurysm. Occlusion of aneurysms by the use of vaso-occlusive coils without occluding the adjacent artery is a special challenge and is a desirable method of reducing such risk of rupture.

As noted above, the use of vaso-occlusive coils in treating aneurysms is widespread. These vaso-occlusive devices are placed in an aneurysm in the following fashion. A microcatheter is initially steered into or adjacent to the entrance of an aneurysm, typically aided by the use of a steerable guidewire. The wire is then withdrawn from the micro catheter lumen and replaced by the vaso-occlusive coil. The vaso-occlusive coil is advanced through and out of the microcatheter. Desirably being completely delivered into the aneurysm. After, or perhaps, during, delivery of such a coil into the aneurysm, there is a specific risk that a portion of the coil might migrate out of the aneurysm entrance zone and into the feeding vessel. The presence of such a coil in that feeding vessel may cause the undesirable response of causing an occlusion there. Also, there is a quantifiable risk that the blood flow in the vessel and aneurysm may induce movement of the coil farther out of the aneurysm, resulting in a more developed embolus in the patent vessel.

One type of aneurysm, commonly known as a "wide neck aneurysm" is known to present particular difficulty in the placement and retention of vaso-occlusive coils. Wide neck aneurysms are herein referred to as aneurysms of vessel walls having a neck or a "entrance zone" from the adjacent vessel, which entrance zone has a diameter that either: (1) is at least 80% of the largest diameter of the aneurysm; or (2) is clinically observed to be too wide effectively to retain vaso-occlusive coils that are deployed using the techniques discussed above.

Furthermore, vaso-occlusive coils lacking substantial secondary shape strength may be difficult to maintain in position within an aneurysm no matter how skillfully they are placed.

There are few disclosed devices for maintaining the presence of vaso-occlusive coils within an aneurysm. One such device is shown in U.S. Pat. No. 08/690,183, filed Jul. 26, 1996 for "ANEURYSM CLOSURE DEVICE ASSEMBLY" (attorney docket 29025-20162.00). That document describes a number of devices all which are said to be placed within the lumen of a feed vessel exterior to the aneurysm so to retain coils within the aneurysm cavity. That is to say that the retainer device is released in the vessel exterior to the aneurysm. The device is held in place via the presence of radial pressure on the vessel wall. After the device is released and set in an appropriate place, a microcatheter is inserted into the lumen behind the retainer device and the distal end of the catheter is inserted into the aneurysm cavity. One or more vaso-occlusive devices is introduced into the aneurysm cavity. The retainer device maintains the presence of those vaso-occlusive devices within the aneurysm no matter whether the aneurysm is a large mouth aneurysm or not.

Another device for closing an aneurysm is found in U.S. patent application Ser. No. 08/588,195, filed Jan. 18, 1996 for "ANEURYSM CLOSURE METHOD" (attorney docket number 29025-20136.00). In this procedure, a vaso-occlusive device such as a coil or braid has on its outer surface a polymeric composition which may be reformed or solidified in situ within the human body. The device is simply inserted into the aneurysm and the polymer is then reformed, e.g., by the application of light, to melt or otherwise to reform the polymer exterior to the vaso-occlusive device. The vaso-occlusive device then sticks to itself at its various sites of contact and forms a rigid whole mass within the aneurysm.

There are a variety of other vaso-occlusive coils and devices which may be specified herein. The material provided above is only exemplary of the patents and publications dealing with such devices. No neck bridge device of the structure described herein is found in any of the references described above.

SUMMARY OF THE INVENTION

This invention includes an implantable medical device. It may be used either for retaining other occlusion devices at an occlusion site, such as an aneurysm, or by itself for forming a bridge over the mouth of the aneurysm. The invention includes related methods of introducing and installing that medical device at the occlusion site. Combinations of the retainer device and its included vaso-occlusive material or device are also an aspect of the invention. In particular, the invention involves an implantable retainer which is deliverable through an elongated tubular delivery device such as a vascular catheter. The implantable retainer or neck bridge. The inventive device typically includes a core wire having both a proximal end and a distal end. At the distal end is a releasable joint which extends between the distal end of that core wire and a first intra-aneurysm section comprising a number of array elements and an optional extra-aneurysm section. The desired joint is electrolytically severable upon application of a suitable current to the joint. The joint may be comparatively more electrolytically dissolvable when a current is applied than any of the rest of the implantable retainer components. The inner aneurysm section of the retainer assembly itself has a number of array elements which may be of a shape (a first or delivery shape) which is deployable through a delivery catheter and, upon exit from the distal end of that catheter, readily assumes a secondary shape desirably conforming to the interior of the aneurysm catheter. Electrolysis of the preferred severable joint then permits placement of the retainer assembly in the aneurysm and removal of the attached delivery apparatus. Optional placement of the vaso-occlusive device to be retained in the aneurysm may then be had by simply introducing the vaso-occlusive device and its delivery tubular member between the array elements in the aneurysm.

The array elements are comprised of formed sections of thin sheet, metallic or plastic. The shapes may be loops or may be arms which simply extend from the joint into the aneurysm cavity. It is within the scope of this invention that the retainer assembly include a number of "exterior" array members making up the optional second or extra-aneurysm section, which members, in general, extend radially from the region of the joint and are intended to remain in the feed vessel—not in the aneurysm—after deployment. These exterior loops define, with the interior array elements an annular area between them into which the rim or mouth of the aneurysm may fit.

The various portions of the device may be made to be radio-opaque by the choice of materials or by such other procedures as by plating the components with a radio-opaque metal, such as gold.

DESCRIPTION OF THE INVENTION

This invention involves a device and procedure for solving the problem of closing the mouths of aneurysms either by stabilizing the structure and placement of vaso-occlusive devices when they are placed in such an aneurysm or by closing the aneurysm mouth by itself. These inventive retaining devices or aneurysm neck bridges may be used to prevent the migration of occlusion devices such as coils from a target occlusion site, by forming a barrier at the entrance zone to the target site from a feeding vessel. The remainder of the retainer device which is remote from the mouth generally provides stability to the portion of the device which resides in the mouth of the aneurysm. The inventive device may be used to close the mouth of the aneurysm by itself.

Figure 1A:
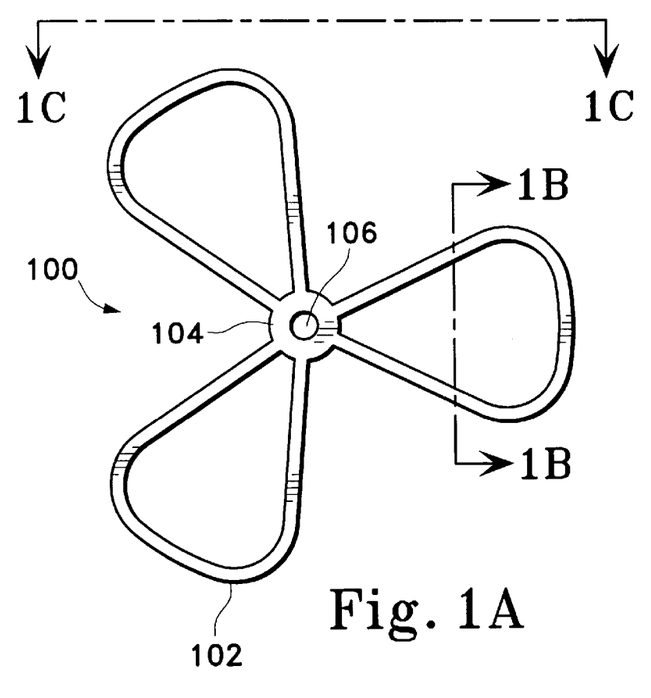
FIGS. 1A, 1B, and 1C are respectively top view, cutaway view, and side view of a variation of the inventive aneurysm retainers.
Figure 1B:
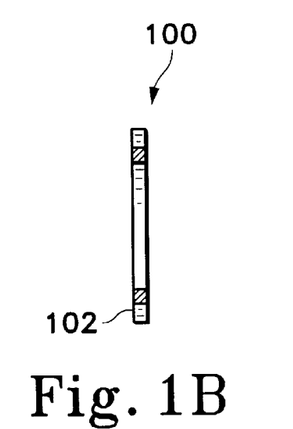
Figure 1C:
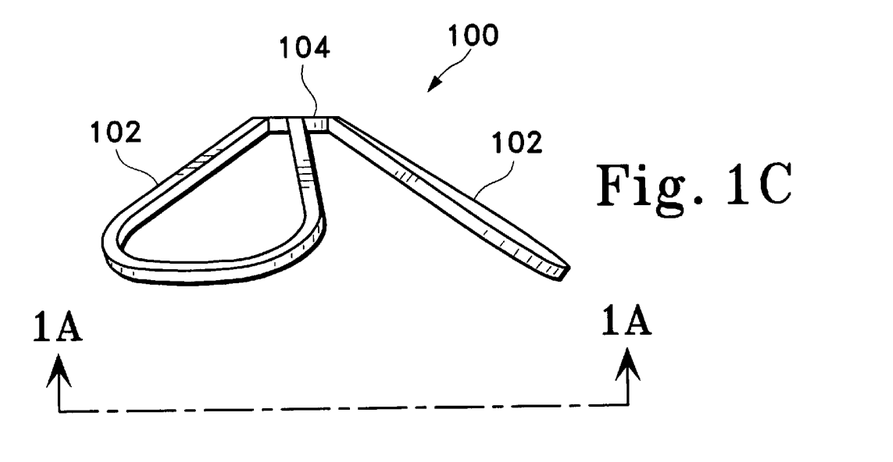

FIGS. 1A, 1B, and 1C show respectively top view, cutaway view, and side view of a typical device made according to the invention. Retainer device (100) as shown in FIG. 1A has an approximate "flower" shape with a number of petals (102). These petals or array elements (102) extend from a center or joining section (104). The center section (104) may (and generally does) have an opening (106) therethrough. As will be shown below, the inventive device (100) itself may be attached to a detachable controllable joint attached, in turn, to a core wire for delivery of the device to a selected site in the body. This "controllable joint" may be electrolytic in nature or mechanical in nature. It will be described in more detail below. The joint itself is included for at least a pair of reasons: (a) to allow proper placement of the inventive device (100) prior to release from control by the physician using the device, (b) if the inventive retainer (100) somehow is malplaced, the core wire and the joint may be used to withdraw the inventive device (100) back into or onto the delivery catheter (or other suitable delivery tubular member) for proper repositioning or removal.

Central to this invention is the fact that the inventive device (100) is made from a sheet material. That is to say, that the device, unlike many others of this class, is not typically made of a wire which is otherwise assembled to make up the retainer. Typically, the inventive device (100) (and the other variations discussed below) are formed from a single integral piece of metal, an alloy, or a polymeric sheet. The cross-section of the inventive device (100) shown in FIG. 1B depicts the sheet metal found in one array element (102) of the device.

FIG. 1C shows in side view, the approximate shape of inventive device (100). The central section (104) and several of the array elements (102) may also be seen. It is not critical to this invention that the natural shape of inventive device (100) be as shown in FIG. 1C. It is, nevertheless, desirable. The device may remain flat. FIG. 1C shows that this variation of the inventive device is what we term a "first section" in that it remains mainly within the aneurysm after deployment. Some portion of central region (104) may be in the neighborhood of the aneurysm mouth but typically would not extend into the patent artery adjacent aneurysm. As will be discussed below, it is within the scope of this invention that the inventive device also have an optional second or exterior section, above the plane of central region (104), which provides some measure of assurance that the inventive device stays in the region of the aneurysm opening. Again, the exterior section will be discussed in isolation below with regard to FIGS. 3A and 3B.

It is to be understood that the shapes shown in most of the figures herein are shapes assumed during the process of manufacture or after ejection of the device into an unconfining region. That is to say that the "natural" shape of the device is as shown in the drawings. The aneurysm itself may have some effect on the shape of the device after the device has been placed into the aneurysm. The sheet or foil used in this device may be polymeric or metallic in nature. It is central to this invention that the device be delivered easily through or upon a vascular catheter. Consequently, the device must be folded or rolled or otherwise shaped into a very small profile to allow its passage through vascular portions of the human body. Such shapes will be discussed in more detail below. Because of the necessary, substantial folding or rolling, it is usually preferable that the whole of the inventive device (100) (and its variations discussed below) be produced of a material such as a super-elastic alloy.

Super-elastic or pseudo-elastic shape recovery alloys are well known. For instance, U.S. Pat. Nos. 3,174,851; 3,351,463; and 3,753,700 each describe one or more of the well known super-elastic alloys, commonly generically known as nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its so-called super-elastic properties. The alloy mentioned in the three patents just above is a nickel-titanium alloy. It is readily commercially available and undergoes the austenitic-SIM-austenitic transformation at a variety of temperatures between −20° C. and +30° C. depending to some extent upon the procedure by which the specific alloy is made.

These alloys are especially suitable because of their capacity to recover elastically, almost completely, to the initial configuration once the stress is removed. Typically, in these services, there is little plastic deformation even at relatively high strains. This allows the retainer device (100) to undertake substantial bends both as it is collapsed to enter the tubular delivery device or system and also as it undertakes further bending and passing through turns into vasculature. In spite of this bending, the material returns to its original shape once the bend in the vasculature has been traversed without retaining any kink or bend.

Although most available super-elastic alloys are acceptable to this service to the extent that they are biocompatible, we prefer material nominally 50.6%∓2% nickel and most of the remainder, titanium. Up to about 5% of the alloy may be another member of the Iron Group of metals, particularly chromium and iron. The alloy should not contain more than about 500 ppm of oxygen, carbon, or nitrogen. The transition temperature of this material is not particularly important, but it should be reasonably below the typical temperature of the human body so to allow to be in its austenitic phase during use. The thickness of the material making up the inventive device may be as much as 0.00001 inches but preferably is 0.002 inches or less. Typical super-elastic alloys are not readily visible under fluoroscopy. Consequently, it is often desirable to add a covering to improve the radio-opacity of the device. Radio-opaque materials such as gold and platinum are well known and may be readily electroplated onto the surface of the inventive device. This modest layer of plating provides substantial radio-opacity.

Although super-elastic alloys are highly desirable in this service, other metals and alloys may, in certain circumstances, be appropriate. Such metals include a number of stainless steels and other highly elastic, if not super-elastic, alloys. Furthermore, it is within the scope of this invention that the array elements (102) be of a polymeric material. Polymeric materials are somewhat easier to work with in forming the device and for maintaining the vaso-occlusive devices at an appropriate site with any aneurysm. Such materials as polyethylene, polypropylene, polytetrafluoroethylene, various Nylons, and the like would easily be chosen by one having ordinary skill in this art for the purposes shown herein.

Figure 2:
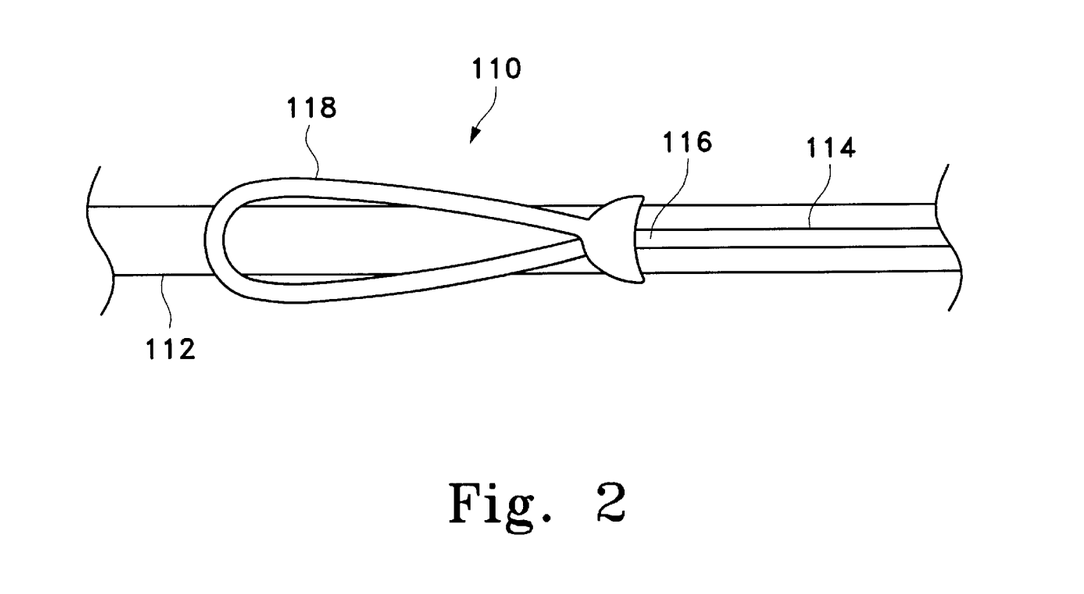
FIG. 2 is a partial side view of a device made according to this invention wrapped around a delivery catheter section.

FIG. 2 shows a device (110) similar in design to the inventive device shown in FIGS. 1A, 1B, and 1C. In this instance, inventive device (110) is wrapped about a delivery catheter (112) for delivery to a site in the human body. The device (110) is shown with a core wire (114) and an electrolytic joint (116) to allow the device (110) to remain in a vicinity of delivery catheter (112) until the person operating the device wishes it to remain in the human body. The electrolytic joint (116) may also be called a sacrificial link. Core wire (114) is typically coated with an electrical insulator which is not susceptible to dissolution by electrolysis in blood or other ionic media. Suitable coatings for core wire (114) include, but are not limited to, such insulating materials as the polyfluorocarbons (e.g., Teflon), polyurethane, polyethylene, polypropylene, polyimides, or other suitable polymeric materials. Polymeric joint (116) is not coated with such an insulator and is of a material which is susceptible to electrolytic dissolution or erosion in blood. Electrolytic joint (116) may be a simple non-insulated continuation of, e.g., stainless steel core wire (114), which has been insulated approximately of electrolytic joint (116). It should be apparent that the sacrificial joint (116) is more susceptible to electrolysis than are the array elements of (118) of device (110). Further discussion of the construction of, the placement of, and other physical details of such a joint may be found in U.S. Pat. No. 5,122,136 to Guglielmi, et al.; U.S. Pat. No. 5,354,295 to Guglielmi, et al; U.S. Pat. No. 5,624,449 to Pham, et al., and others.

Although each of the array elements (102) shown in FIG. 1A is regular and of the approximate same shape as the other array elements on the device, such obviously need not be the case. It is within the scope of this invention that the retainer assembly ((100) in FIG. 1) may be irregular in shape (e.g., not a mirror image across some axis of the device) so to fit the shape of an irregular aneurysm. Placement of such devices must be done with some care, but it is within the purview of one having ordinary skill in this art after some instruction.

Figures 3A, 3B:
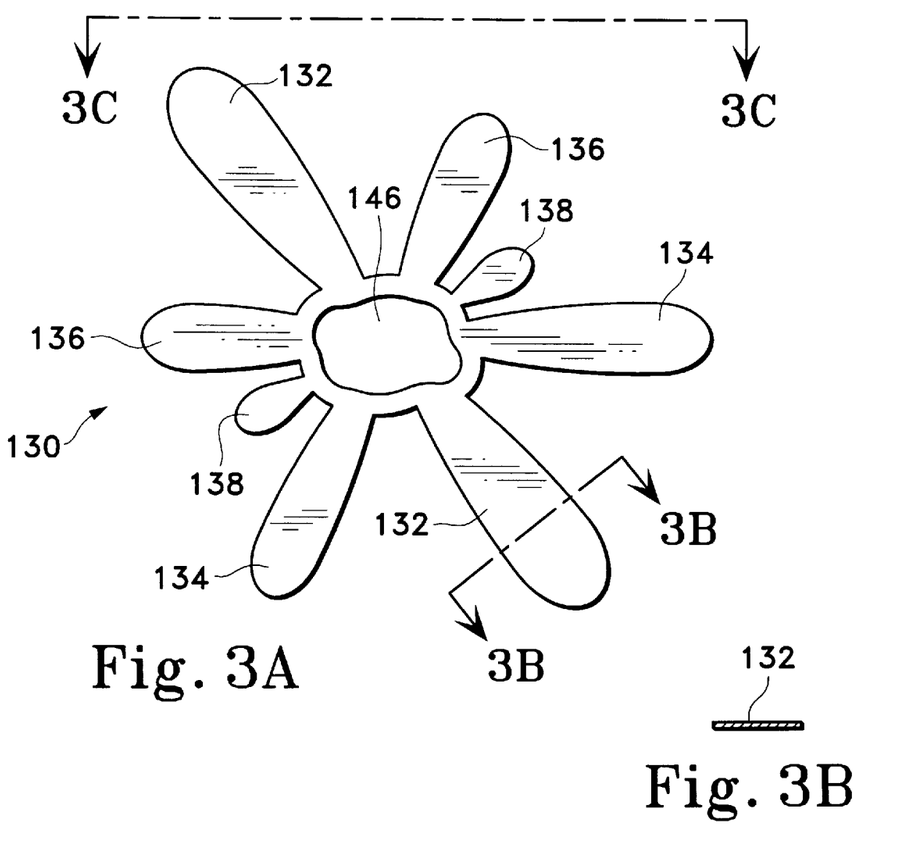
FIGS. 3A, 3B, and 3C are respectively top view, cross-section, and side view of a variation of the inventive aneurysm retainers.
Figure 3C:
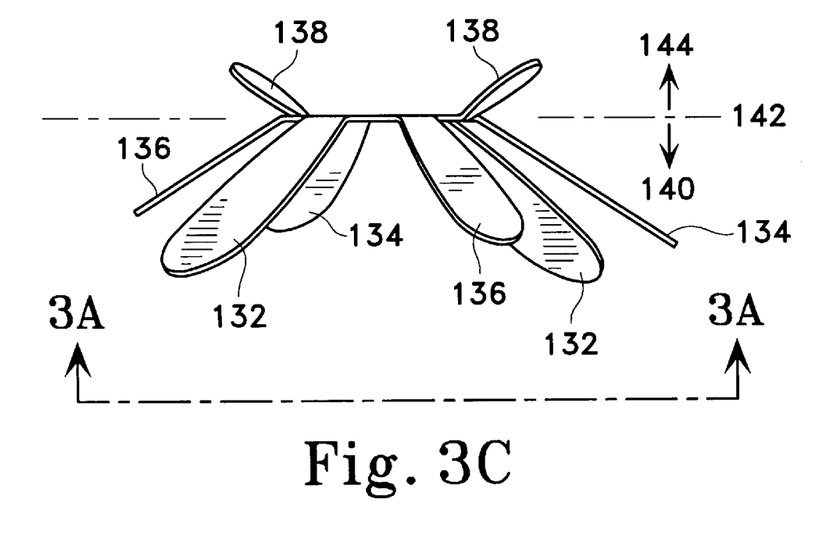

Similarly, FIGS. 3A, 3B, and 3C show a variety of independent concepts suitable for use in the device of this invention. Specifically, and in contrast to the array elements (102) shown in FIG. 1, the array elements shown in FIGS. 3A and 3C are not "hollowed" but are wider portions of sheet or foil. Secondly, the array elements are not regular. Finally, the inventive device (130) shown has both an inner section for placement within the aneurysm and an outer section for situs outside the interior of the aneurysm. Each of these concepts may be independently applied to variations of the inventive aneurysm neck bridge.

FIG. 3A shows an inventive neck bridge device having array elements (132) which are larger than adjacent elements (134) and still larger than adjacent array elements (136). Note that the respective side array elements are not necessarily placed on a single diameter across the device.

Array elements (132, 134, and 136) constitute the so-called inner section of the device. This inner section is shown in FIG. 3C as (140) below axis line (142) also shown in FIG. 3C. The outer portion is the region of the device (144) above axis line (142) in FIG. 3C. In this variation of the device, only array elements (138) are in the outer section.

FIG. 3B is merely a cross-section of one of the array members (132) and it depicts the concept that the array element in this instance is a continuous one which, in contrast to the cross-section of array element (102) shown in FIG. 1B, does not have a hollowed center. This variation may have some advantages in that after placement of the device in the manner shown below in the opening of an aneurysm, the amount of coverage or the relative percentage of the aneurysm mouth covered by the neck bridge is comparatively quite high. Such a variation may not always be useful in maintaining vaso-occlusive devices such as helical coils within an aneurysm. In some instances, the more sparse device shown in FIGS. 1A, 1B, and 1C may be highly suitable and the best choice. It should be apparent that the device shown in the former figures is significantly more flexible than the variation shown in FIGS. 3A, 3B, and 3C, at least to the extent that the devices are of similar size, of course.

Another improvement which will be discussed below is the irregular shape of the center opening (146).

Opening (146) is irregularly shaped for several reasons. One reason is to minimize or to provide, at least, an appropriate amount of torque to the various array members (132, 134, 136, 138) and provide a measure of safety for the device when properly placed in an aneurysm neck. The other reason is for minimization of the thickness of the periphery of opening (146) in such a way that when folded or collapsed prior to the deployment step, the metal around the periphery of the opening (146) doesn't overlap or form a fluted cone about its central opening.

Figure 4:
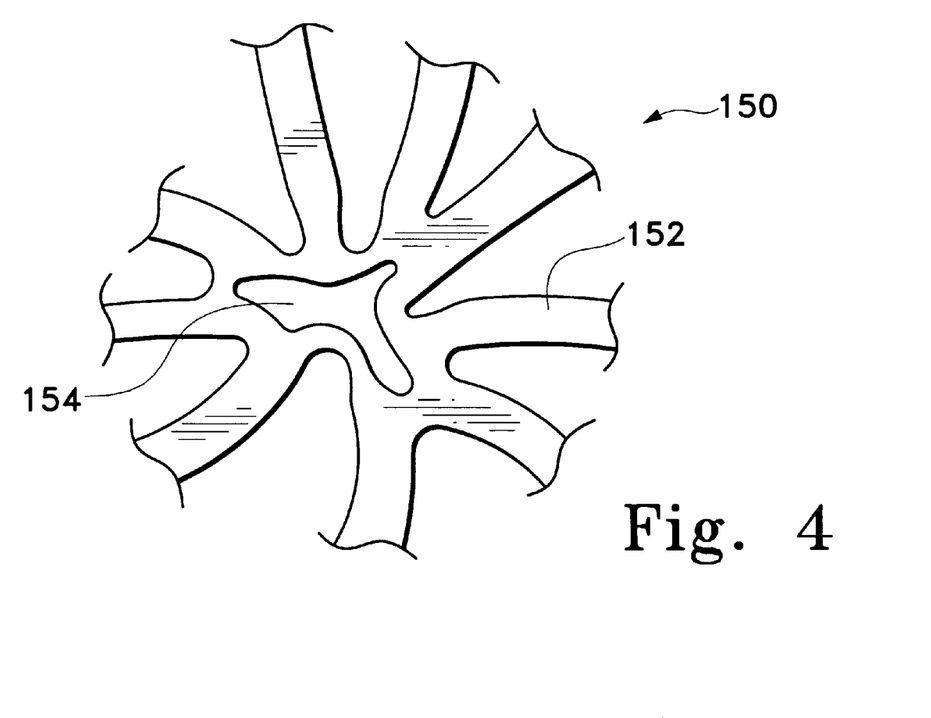
FIG. 4 is a partial top view of a central section of the inventive device.

FIG. 4A shows a central portion of a device (150) which is similar to that shown in FIGS. 3A, 3B, and 3C. It has a number of array elements (152) which may form either an inner section or an outer section as was discussed above in relation to FIGS. 3A, 3B, and 3C. Inventive device (150) has a central opening (154) which is irregular in shape but is tailored to minimize thickness when folded about open area (154). Because the center of device (150) is not, in this variation, centered about a single point which necessarily forms the point about which the device will fold. Consequently, the device may be folded along a number of lines perpendicular to the plane of the drawing in FIG. 4 so to minimize the thickness of the device around the fold point and enhance its resulting flexibility.

Figure 5:
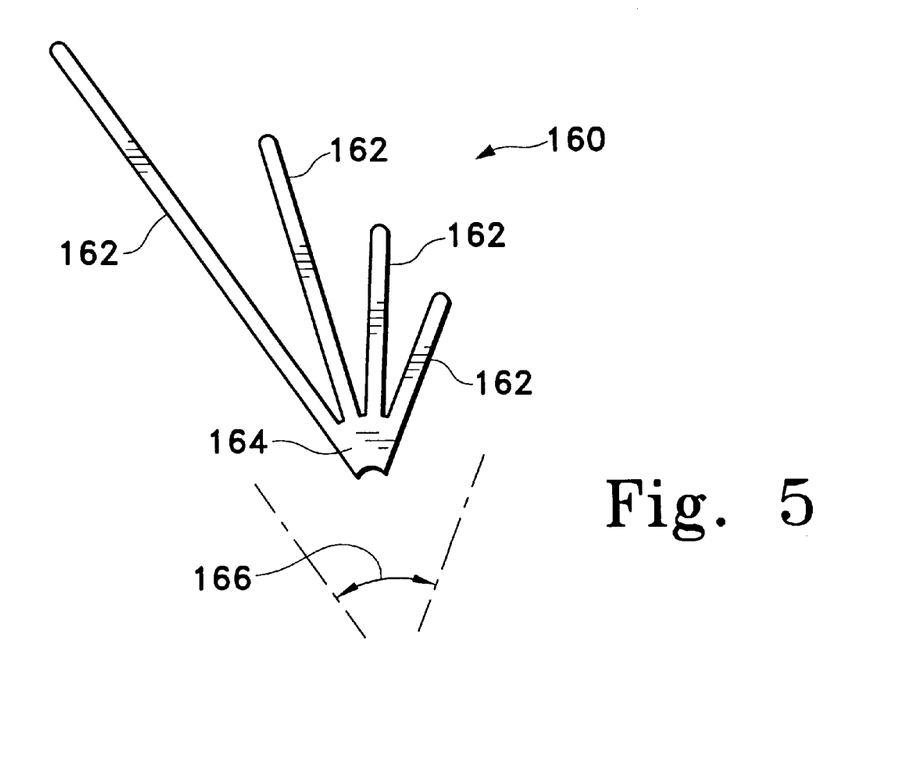
FIG. 5 is a top view of a variation of the inventive aneurysm retainer.

FIG. 5 shows another variation (160) of the inventive device. This device includes a number of array elements (162) of varying lengths. Each is attached to a connective platform region (164). Platform region (164) may in turn be connected to a delivery joint much in a manner discussed above. In this variation of the inventive device, a number of devices (160) shown in FIG. 5 may be placed in an aneurysm with connective field (164) situated at or near the aneurysm mouth. The various array members (162), although shown to be having a number of lengths, they may be of the same length. The angle (166) shown in FIG. 5 typically is not more than about 90°. The device (164) shown in FIG. 5 is depicted as flat although it may have a slight curve, at least partially, to match the interior of the aneurysm. Placement of a number of these devices within an aneurysm allows the device (160) to be used in conjunction with other similar devices to more appropriately control the retention of vaso-occlusive devices such as helical coils within the aneurysm, particularly when the aneurysm is not regular or berry-like in shape.

Figure 6:
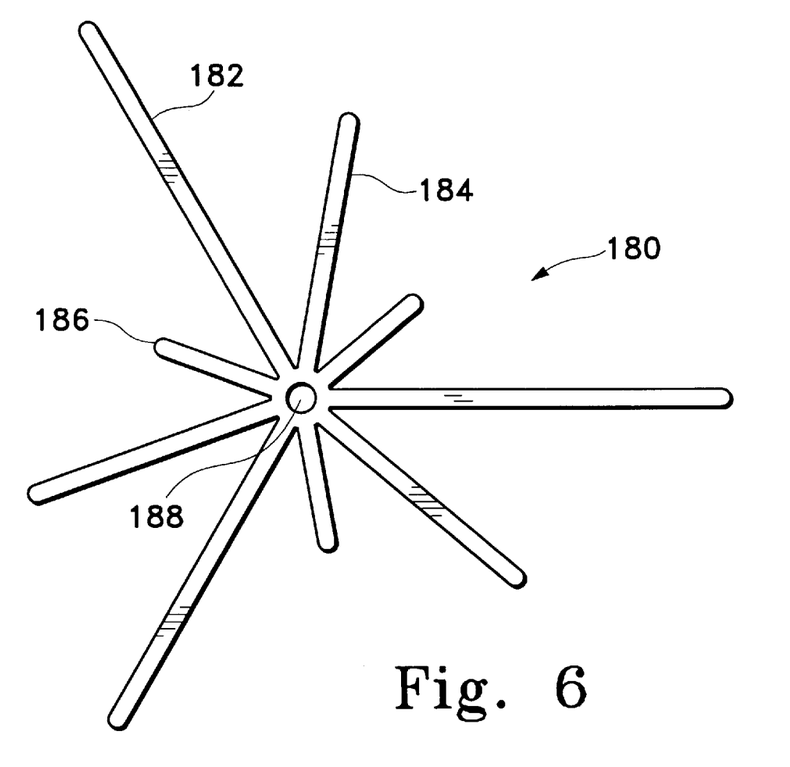
FIG. 6 is a top view of a variation of the inventive aneurysm retainer.

FIG. 6 shows still another variation (180) of the inventive device. This variation includes a number of longer array elements (182), medium-sized array elements (184), and shortest array elements (186). This variation depicts a round central open area (188). It is within the scope of this invention that the shorter array elements (186) may be configured by the user or manufacturer either to form a portion of the inner section discussed above which is situated within the aneurysm or may be formed in such a fashion that the shorter array elements (186) are situated outside the aneurysm neck. Again, the walls and neck of an aneurysm are typically indescribably fragile and consequently use of an outer section is typically not desired.

This variation (180) of the inventive device may also be configured with an irregular central open area as has been discussed above. It should be observed that the materials which are used to make up this device are by their very nature, quite thin and may be machined using high pressure water jets and the like. Consequently, computer-assisted design and manufacturing (CAD/CAM) may be used to a great advantage in producing these devices. Quite obviously, they may also simply be punched using normal dies. It is highly desirable to round or smooth the edges to prevent snagging and tearing of the intima.

As noted above, the thickness of the materials making up the device is likely no more than about 10 mils, preferably less than 6 mils and most preferably from 0.5 mils to 2.5 mils. The overall diameter of the device in any direction is rarely more than ¼" when used in the neurovasculature. When placed in aneurysms in larger vessels, as may be found in the periphery or around the heart, the device may be appropriately sized to fit the mouth of the aneurysm to be closed.

Figure 7:
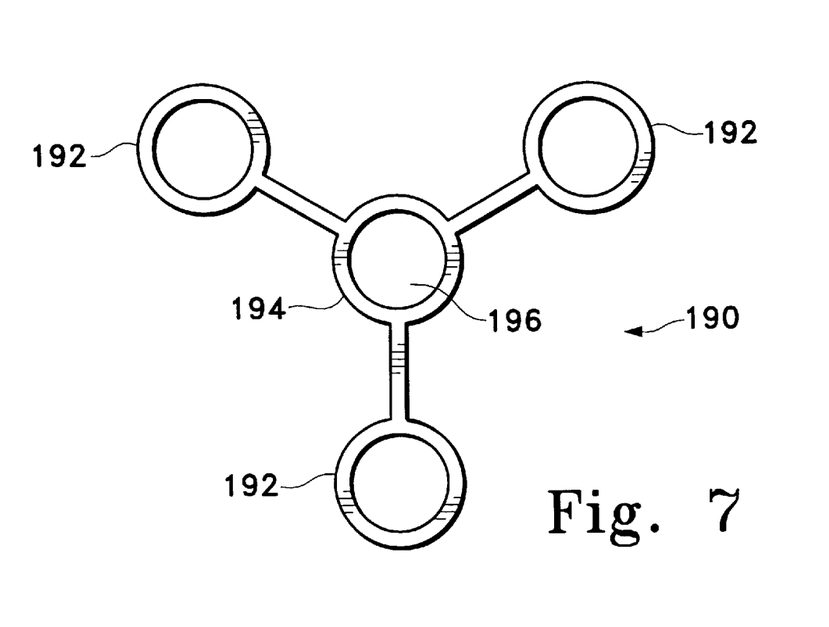
FIG. 7 is a top view of a variation of the inventive aneurysm retainer.

FIG. 7 shows a further variation (190) of the inventive device in which the array members (192) are shaped much like a tennis racquet. The central or joining region (194) of the device (190) has a large opening (196). This device is quite flexible and provides significant contact with the inner aneurysm wall for significant placement stability whether used with vaso-occlusive devices or not.

It should be apparent from a review of this disclosure that the devices of this invention are of a size, shape, and flexibility that they do not cause significant trauma when placed in the mouth of an aneurysm.

Figure 8A:
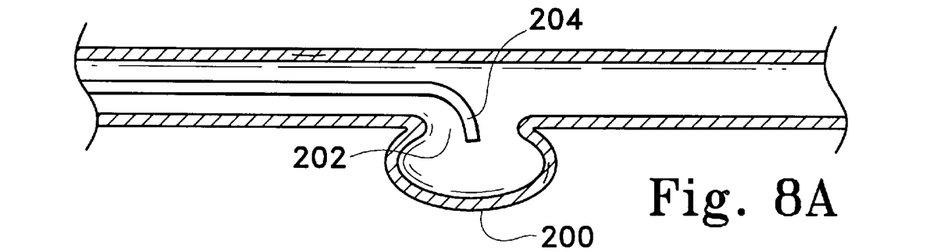
FIGS. 8A to 8E show a method of deploying a device made according to this invention and the vaso-occlusive devices into an aneurysm.
Figure 8B:
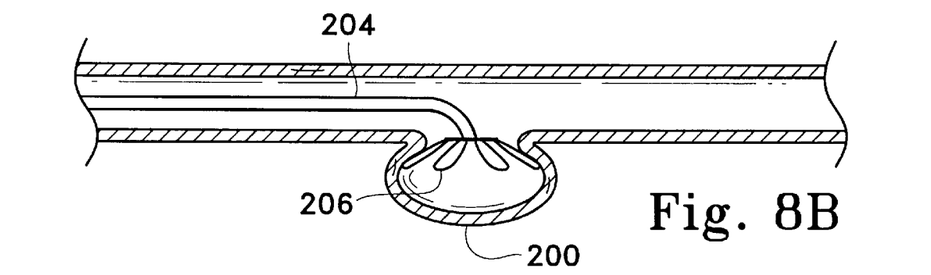

FIGS. 8A through 8E show a way in which the device may be deployed. FIG. 8A shows an aneurysm (200) with a fairly wide neck (202). Entering the mouth (202) is a delivery catheter (204). In this variation of the invention, the delivery catheter (204) has the inventive device (206) inside its interior lumen. The inventive neck bridge (206) is pushed from the delivery catheter (204) and released from the internal pushing apparatus discussed above. Delivery catheter (204) is then removed. Depending upon the decision of the physician delivering the device (206), the procedure may then be stopped. The neck bridge (206) may simply be used to close the aneurysm (200).

Figure 8C:
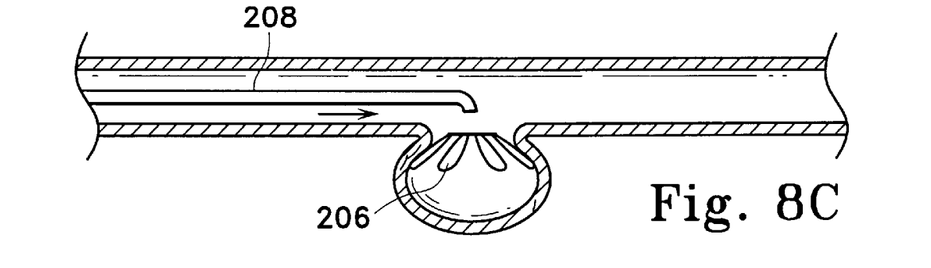
Figure 8D:
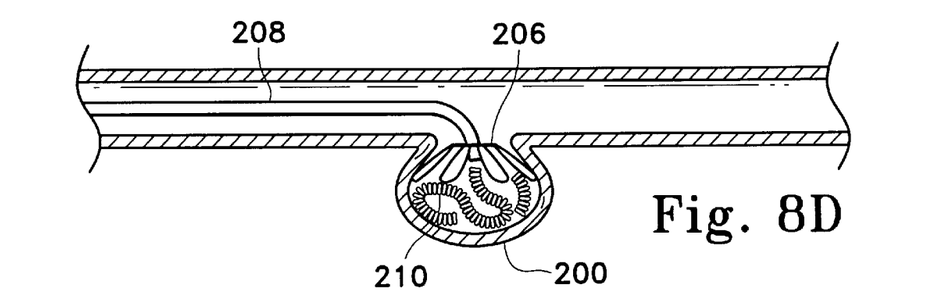

In the preferred use of the inventive concept, the neck bridge (206) is used to maintain other vaso-occlusive devices in the aneurysm.(200). To so place the vaso-occlusive devices, as is shown in FIG. 8C, a second catheter (208) is then delivered to the inventive device (206) and may be placed in the central open region of the device (206) (not seen in this view). Open region (206) is analogous to open region (106) in FIG. 1B, open region (146) in FIG. 3B, and open region (154) in FIG. 4A. A number of vaso-occlusive coils (210) are then placed within aneurysm (200). Neck bridge (206) prevents vaso-occlusive coils (210) from passing out of the aneurysm (200) and into the flowing patent blood stream adjacent to aneurysm (200).

Figure 8E:
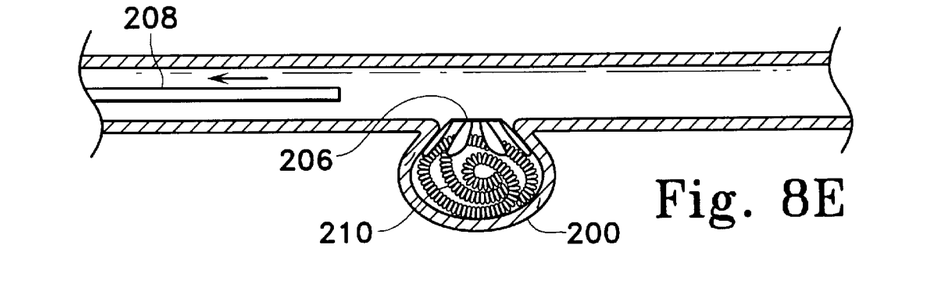

Finally, as shown in FIG. 8E, coil delivery catheter (208) is withdrawn leaving the implanted coils (210) and the inventive neck bridge (206) in a safe and occluding site within aneurysm (200).

Depending upon the size of the inventive device (206) and the coils (210), it may be desirable, and indeed is preferred, to use a single delivery catheter. That is to say that, for instance, neck occlusion device (206) may be placed on the outside of catheter (204) in such a way that catheter (204) extends through the center open region of inventive device (206). After placement of neck bridge (206) in the aneurysm neck, the delivery catheter (204) then remains within the open region of the neck bridge (206). The neck bridge (206) stays attached to the delivery catheter (204) or pusher. The coils are then easily delivered through delivery catheter (204) and through the open region of neck bridge (206). The neck bridge (206) is then detached from the delivery catheter or pusher.

It should be apparent that because of the fairly open nature of the devices made according to this invention, that vaso-occlusive coils and similar devices need not be delivered directly into a central open area but may delivered through or between the various array arms of the device.

Figure 9:
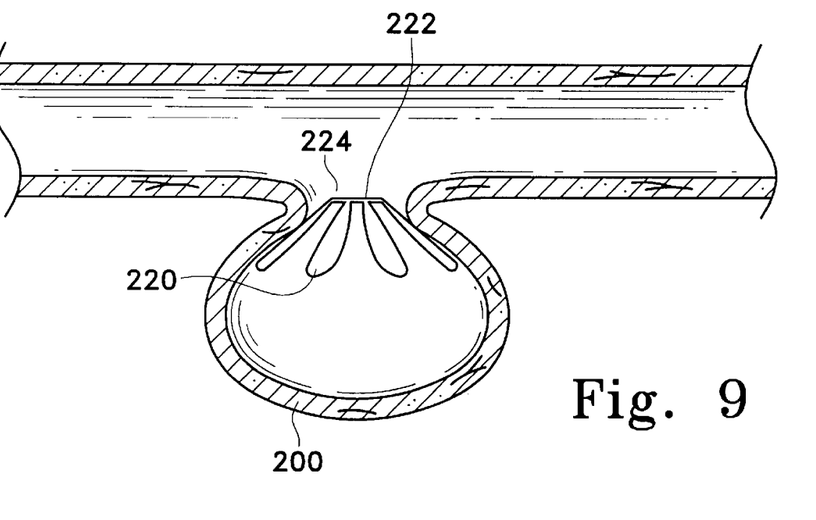
FIGS. 9 and 10 show placement of two different variations of the invention in aneurysms.
Figure 10:
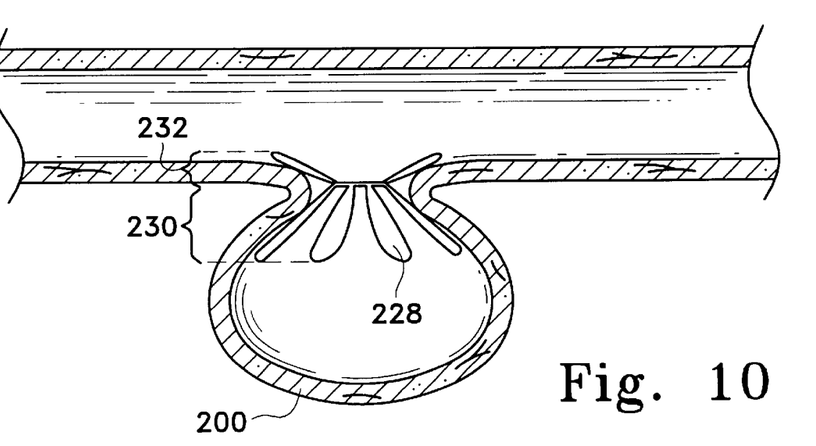

FIGS. 9 and 10 depict placement of, respectively, inventive devices having only an inner section and having both an inner section and an outer section in an aneurysm (200).

FIG. 9 shows an aneurysm (200) into which a neck bridge (220) has been properly placed. This neck bridge (220) has only an inner section as was discussed above with regard to the variations in FIGS. 3A, 3B, and 3C. In FIG. 9, the central section (222) sits in the neighborhood of the mouth (224) of the aneurysm. It, however, does not extend typically out into the adjacent vessel. Again, this device may be used to close the aneurysm (200) without the additional introduction of vaso-occlusive devices into the aneurysm.

FIG. 10 shows the variation of the inventive device (228) having both interior section (230) and exterior section (232).

The device has been properly placed within the mouth of the aneurysm (200). It is preferred that the exterior section (232), however, not extend significantly out into the vessel. This permits, however, one to be relatively certain that the neck bridge stay in place either when used as a sole neck bridging device or, when used in conjunction with vaso-occlusive devices, during the later steps of including those vaso-occlusive devices.

Many alterations and modifications may be made by those of ordinary skill in this art, without departing from the spirit and scope of this invention. The illustrated embodiments have been shown only for the purposes of clarity and the examples should not be taken as limiting the invention as found in the following claims, which claims are intended to include all equivalents, whether now or later devised.

We claim as our invention:

1. An implantable neck bridge, deliverable via an elongate tubular delivery device, of a size and flexibility capable of at least partially closing the mouth of a vascular aneurysm, comprising a plurality of array elements and a joining region, where said array elements and said joining region are both formed from a single sheet of material, said array elements being elongated and each having a free end and an end attached to said joining region, and wherein the device is substantially planar.

2. The device of claim 1 wherein the joining region has an opening therethrough.

3. The device of claim 1 wherein at least some of the array elements have openings therethrough.

4. The device of claim 2 wherein the opening is irregular.

5. The device of claim 1 wherein the joining region is substantially centrally located amongst said array elements.

6. The device of claim 1 wherein the device is bent into a first and a second substantially non-planar regions.

7. The device of claim 6 wherein all of the array elements are bent in a same direction on a single side of the joining region to form said first non-planar region.

8. The device of claim 6 wherein the array elements are bent in two substantially opposite directions from said joining region to form said first and second non-planar regions.

9. The device of claim 1 further comprising in combination adjacent at least said joining region, at least one vaso-occlusive device.

10. The device of claim 9 wherein said at least one vaso-occlusive device is a helically wound coil.

11. The device of claim 1 wherein said sheet material is metallic, polymeric or super-elastic alloy.

* * * * *